Figure 2:
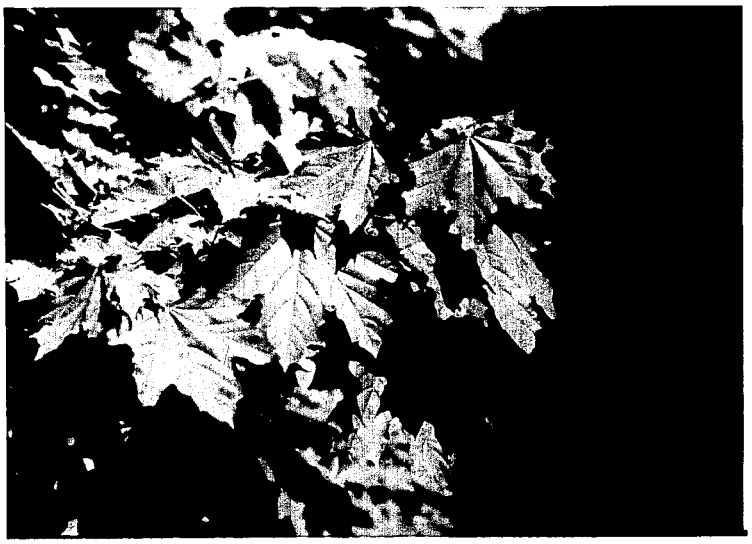

United States Patent [19]

Flemer, III

[11] Patent Number: Plant 6,727

[45] Date of Patent: Apr. 11, 1989

[54] PRINCETON GOLD

[75] Inventor: William Flemer, III, Princeton, N.J.

[73] Assignee: New Plant Associates, Princeton, N.J.

[21] Appl. No.: 105,271

[22] Filed: Oct. 5, 1987

[51] Int. Cl.[4] ..... A01H 5/00

[52] U.S. Cl. ..... Plt./51

[58] Field of Search ..... Plt./51

*Primary Examiner*—Robert E. Bagwill

*Attorney, Agent, or Firm*—Frank B. Robb

[57] ABSTRACT

A Norway Maple, Acer platanoides, denominated "Princeton Gold", which displays a bright yellow foliage as the outstanding feature of appearance, as compared with the leaves of other seedlings which are of a normal green color, the bright yellow persisting throughout the summer months and resistant to sun scorching or burning, asexual reproduction establishing the characteristics as continuing from generation to generation.

1 Drawing Sheet

During my continuing and broad scale development and observation of various kinds of plants and many of these being trees of a decorative nature, which are grown and observed at nurseries in Plainsboro Township, N.J., I have learned to select outstanding varieties and in this instance a maple tree known as Acer platanoides. I have chosen to designate this variety as "Princeton Gold" for the purposes of this description and in use in commerce.

Since a large number of trees of the Norway Maple variety are grown in the nurseries referred to, I am continually observing the various trees individually and thus the particular tree of this application, Acer platanoides, Norway Maple, came to my attention.

This particular tree was first noticed in a bed of Norway Maple seedlings which had originated from seed which were collected along the streets of the town of Princeton, N.J., this being a project to which I have devoted considerable energy since it is desirable to provide seedlings and growing trees which may be grown in cities and without producing a large amount of litter, at the same time be attractive and thus add to the pleasantness of city life in general.

This particular variety was easily noticed because of its bright golden leaves, compared to the leaves of other seedlings which are of the usual or normal green color. This tree, which was found in the bed of Norway Maple seedlings, was transplanted to a stock block and grown on for further observation. Since the bright yellow foliage returned each year and maintained its color throughout the summer months, it was particularly important to note that it did so without sun scorching or burning which is characteristic of so many yellow foliaged trees under American conditions.

I have caused the variety to be reproduced asexually by bud grafting and the grafted trees maintain the same yellow leaf color thus establishing that the same will continue to do so from generation to generation.

The trees have grown with good vigor reaching a height of six feet at the end of the first growing season after the seedlings were cut back to the bud.

In the specific description which I have set forth herein and which follows hereafter, there are certain of the specifically notable characteristics referred to and enable the tree to be distinguished from other varieties. The most particular distinction is in the bright yellow color of the leaves and as they continue to grow, they do so without scorching or burning which takes place where yellow foliaged trees are grown a fact which is recognized in the trade.

Figure 1:
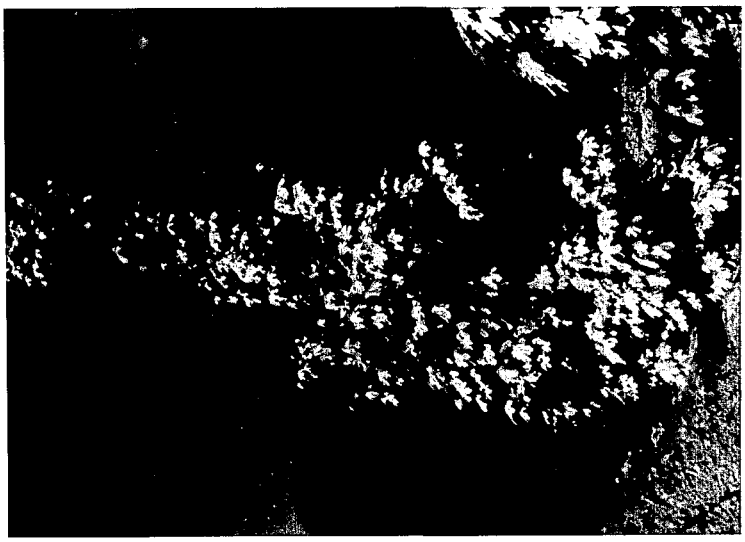

In the drawing which is appended hereto, I have shown in FIG. 1 a view of the tree itself to illustrate its shape and to suggest the color.

In the FIG. 2 disclosure, larger in detail, the same discloses the yellow color which I have referred to and which is important in my judgment.

A detailed description of the invention is now set forth as follows:

Seed parent: Not known.

Pollen parent: Not known.

Newly found seedling of: Acer platanoides, Norway Maple.

Tree: Small; spreading; medium low; hardy.

*Trunk.*—Stocky and smooth.

*Branches.*—Stocky and smooth. Color — Light olive; Munsell Color Chart 5Y 5/6 Lenticels — Sparse; minute; 6 to 8 cm. on the twig.

*Leaves.*—Abundant, with shiny under surface. Length — 11 to 13 cm. Width — 15 to 18 cm. Shape — Palmate, sharply lobed, 5 major lobes, wider than long. Color — Vivid yellow; Munsell Color Chart 2.5Y 8/12. Margin — Lobed, with acuminate lobes, widely dentate with pointed teeth. Petiole — Short; 5 to 6 cm. long. Glands — None. Stipules — None.

Flower buds: Not significant.

Flowers: Not significant; borne in many flowered clusters.

*Date of first bloom.*—April 15th.

*Full bloom.*—April 20th.

*Quantity.*—Sparse.

*Size.*—Medium.

Petalage: Not significant.

*Color.*—Strong greenish yellow; Munsell Color Chart 10Y 8/11.

Fruits: Paired samaras with opposite horizontally spreading wings.

*When borne.*—Ripen in late October.

*Abundance.*—Not abundant.

*Size.*—5 cm. long; 1.2 cm. wide.

*Color.*—Pale brown.

I claim:

1. A new and distinct variety of Norway Maple tree substantially as herein shown and described, characterized particularly as to novelty by the unique combination of the bright yellow foliage which foliage remains bright yellow throughout summer months and which yellow foliage is retained without sun scorching or burning during this period, the other characteristics being substantially similar to the usual Norway Maple, but rapid growth being an attribute which is of value in such trees of ornamental nature.

* * * * *